United States Patent [19]

Takahashi et al.

[11] Patent Number: 5,322,835
[45] Date of Patent: Jun. 21, 1994

[54] N-PHENYLIMIDES, AND THEIR PRODUCTION AND USE

[75] Inventors: Junya Takahashi; Masayuki Enomoto, both of Hyogo; Toru Haga; Masaharu Sakaki, both of Osaka; Ryo Sato, Tokyo, all of Japan

[73] Assignee: Sumitomo Chemical Company, Limited, Osaka, Japan

[21] Appl. No.: 337,406

[22] Filed: Apr. 13, 1989

[30] Foreign Application Priority Data

| | | | |
|---|---|---|---|
| Apr. 20, 1988 | [JP] | Japan | 63-98590 |
| Apr. 20, 1988 | [JP] | Japan | 63-98591 |
| Jul. 5, 1988 | [JP] | Japan | 63-167924 |
| Feb. 16, 1989 | [JP] | Japan | 1-37855 |

[51] Int. Cl.$^5$ .................. C07D 417/14; A01N 43/78
[52] U.S. Cl. ................ 504/225; 504/221; 504/267; 504/270; 544/51; 544/52; 544/105; 548/162; 548/217
[58] Field of Search .......... 71/88, 90, 92, 95; 544/58.4, 105, 51, 52; 548/221, 159, 165, 169, 170, 173

[56] References Cited

U.S. PATENT DOCUMENTS

| | | | |
|---|---|---|---|
| 4,640,707 | 2/1987 | Nagano et al. | 548/221 |
| 4,720,297 | 1/1988 | Haga et al. | 548/161 |
| 4,786,310 | 11/1988 | Hagg et al. | 71/90 |
| 4,804,400 | 2/1989 | Moser | 548/549 |
| 4,818,272 | 4/1989 | Hirai et al. | 71/88 |
| 4,902,335 | 2/1990 | Kume | 546/270 |
| 4,902,337 | 2/1990 | Hirai | 548/321.1 |
| 4,964,905 | 10/1990 | Kouji | 544/143 |

FOREIGN PATENT DOCUMENTS

| | | |
|---|---|---|
| 0190755 | 2/1986 | European Pat. Off. . |
| 0262428 | 9/1987 | European Pat. Off. . |
| 311135 | 4/1989 | European Pat. Off. . |
| 0328001 | 8/1989 | European Pat. Off. . |
| 62-174065 | 7/1987 | Japan . |

OTHER PUBLICATIONS

Ooms et al. "Preparation of (N-heterocyclophenyl-)-alkylidene dioxoazole as herbicides" CA 115:29351u (1991).

*Primary Examiner*—C. Warren Ivy
*Assistant Examiner*—Celia Chang
*Attorney, Agent, or Firm*—Birch, Stewart, Kolasch & Birch

[57] ABSTRACT

A compound of the formula:

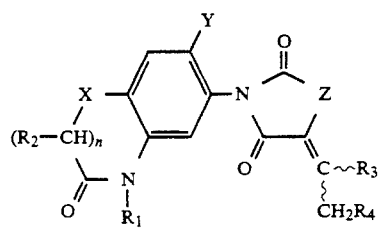

wherein X is an oxygen atom or a sulfur atom, Y is a hydrogen atom or a fluorine atom, Z is a methylene group or a group of the formula: N—R$_5$ (in which R$_5$ is a hydrogen atom, a C$_1$–C$_6$ alkyl group, a C$_3$–C$_7$ alkenyl group, a C$_3$–C$_7$ alkynyl group, a halo(C$_2$–C$_6$)alkyl group or a C$_1$–C$_6$ alkoxycarbonylmethyl group), R$_1$ is a hydrogen atom, a C$_1$–C$_6$ alkyl group, a C$_3$–C$_7$ alkenyl group, a C$_3$–C$_7$ alkynyl group, a halo(C$_2$–C$_6$)alkyl group, a halo(C$_3$–C$_7$)alkenyl group, a cyano(C$_1$–C$_6$)alkyl group, a C$_1$–C$_6$ alkoxy(C$_1$–C$_6$)alkyl group or a C$_1$–C$_6$ alkoxycarbonylmethyl group, R$_2$ is a hydrogen atom or a C$_1$–C$_6$ alkyl group; R$_3$ and R$_4$ are, the same or different, each is a hydrogen atom or a C$_1$–C$_6$ alkyl group; n is an integer of 0 or 1, which is useful as a herbicide.

8 Claims, No Drawings

N-PHENYLIMIDES, AND THEIR PRODUCTION AND USE

The present invention relates to N-phenylimides, and their production and use. More particularly, the present invention relates to novel N-phenylimides, a process for producing them and their use as herbicides. Additionally, the present invention relates to intermediates for producing said N-phenylimides and a process for producing the intermediates.

JP-A-62174065, EP-A-0262428 and EP-A-0190755 disclose several N-phenylimides useful as herbicides. Also, U.S. Pat. No. 4,640,707 discloses several oxazines useful as herbicides and U.S. Pat. No. 4,720,297 discloses several thiazolones useful as herbicides. However, these known herbicides are not sufficient in herbicidal potency or have poor selectivity between crop plants and weeds. Their herbicidal activity is thus not necessarily satisfactory.

It has now been found that N-phenylimides of the formula:

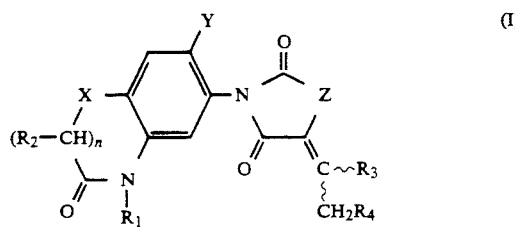

wherein
X is an oxygen atom or a sulfur atom;
Y is a hydrogen atom or a fluorine atom;
Z is an oxygen atom, a methylene group or a group of the formula: N—$R_5$ (in which $R_5$ is a hydrogen atom, a $C_1$–$C_6$ alkyl group, a $C_3$–$C_7$ alkenyl group, a $C_3$–$C_7$ alkynyl group, a halo($C_2$–$C_6$)alkyl group or a $C_1$–$C_6$ alkoxycarbonylmethyl group);
$R_1$ is a hydrogen atom, a $C_1$–$C_6$ alkyl group, a $C_3$–$C_7$ alkenyl group, a $C_3$–$C_7$ alkynyl group, a halo($C_2$–$C_6$)alkyl group, a halo($C_3$–$C_7$)alkenyl group, a cyano($C_1$–$C_6$)alkyl group, a $C_1$–$C_6$ alkoxy($C_1$–$C_6$)alkyl group or a $C_1$–$C_6$ alkoxycarbonylmethyl group;
$R_2$ is a hydrogen atom or a $C_1$–$C_6$ alkyl group;
$R_3$ and $R_4$ are, the same or different, and each is a hydrogen atom or a $C_1$–$C_6$ alkyl group; and
n is an integer of 0 or 1, show a high herbicidal potency against various weeds with a high selectivity between crop plants and weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, wheat, barley, rice plant, soybean, cotton and sugar beet. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), tall morningglory (*Ipomoea purpurea*), field bindweed (*Convolvulus arvensis*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), etc. Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of the Commelinaceous weeds include asiatic dayflower (*Commelina communis*), etc. Examples of the Cyperaceous weeds include purple nutsedge (*Cyperus rotundus*), etc.

The N-phenylimides (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirpus juncoides*) and needle spikerush (*Eleocharis acicularis*), and others such as monochoria (*Monochoria vaginalis*) and arrowhead (*Sagittaria pygmaea*) without producing any phytotoxicity to rice plants on flooding treatment.

Among the N-phenylimides (I), preferred are those wherein X is an oxygen atom or a sulfur atom, Y is a fluorine atom, Z is an oxygen atom or a methylene group, $R_1$ is a $C_1$–$C_4$ alkyl group, an allyl group or a propargyl group, $R_2$ is a hydrogen atom, $R_3$ is a methyl group, $R_4$ is a hydrogen atom and n is an integer of 0 or 1. More preferred are those wherein X is an oxygen atom or a sulfur atom, Y is a fluorine atom, Z is an oxygen atom or a methylene group, $R_1$ is a $C_1$–$C_4$ alkyl group, an allyl group or a propargyl group, $R_2$ is a hydrogen atom, $R_3$ is a methyl group, $R_4$ is a hydrogen atom and n is an integer of 0 or 1, with the proviso that n is an integer of 1 when X is an oxygen atom and n is an integer of 0 when X is a sulfur atom. Typical examples of the preferred compounds are as follows:

3-[7-Fluoro-4-ethyl-2H-1,4-benzoxazin-3(4H)-on-6-yl]-5-isopropylidene-1,3-oxazolidine-2,4-dione;
3-[7-Fluoro-4-isopropyl-2H-1,4-benzoxazin-3(4H)-on-6-yl]-5-isopropylidene-1,3-oxazolidine-2,4-dione;
3-[7-Fluoro-4-propargyl-2H-1,4-benzoxazin-3(4H)-on-6-yl]-5-isopropylidene-1,3-oxazolidine-2,4-dione;
6-Fluoro-5-(5-isopropylidene-1,3-oxazolidine-2,4-dion-3-yl)-3-sec-butyl-2(3H)-benzothiazolone;
6-Fluoro-5-(5-isopropylidene-1,3-oxazolidine-2,4-dion-3-yl)-3-allyl-2(3H)-benzothiazolone;
6-Fluoro-5-(5-isopropylidene-1,3-oxazolidine-2,4-dion-3-yl)-3-propargyl-2(3H)-benzothiazolone;
N-[7-Fluoro-4-methyl-2H-1,4-benzoxazin-3(4H)-on-6-yl]teraconimide;
N-[7-Fluoro-4-propyl-2H-1,4-benzoxazin-3(4H)-on-6-yl]teraconimide;
N-[7-Fluoro-4-propargyl-2H-1,4-benzoxazin-3(4H)-on-6-yl]teraconimide, etc.

The N-phenylimides (I) of the invention can be produced by one of the following procedures:

Procedure (A)

A compound of the formula:

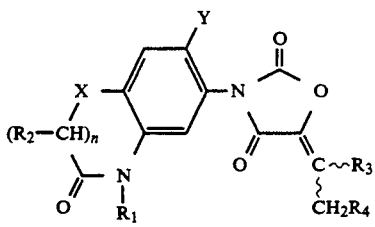

(I-1)

wherein X, Y, R$_1$, R$_2$, R$_3$, R$_4$ and n are each as defined above is prepared by subjecting a compound of the formula:

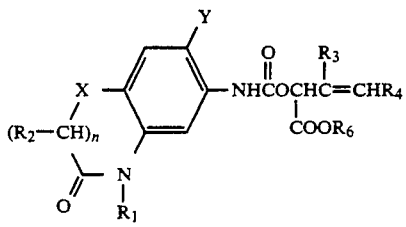

(II)

wherein R$_6$ is a C$_1$-C$_6$ alkyl group and X, Y, R$_1$, R$_2$, R$_3$, R$_4$ and n are each as defined above to ring closure in the presence of a base.

The reaction for ring closure is usually performed in an inert solvent at a temperature of about 0° to about 200° C. for a period of about 1 to about 24 hours. As the base, there may be used sodium methylate, DBU (1,8-diazabicyclo[5.4.0]undec-7-ene), etc. The amount of the base as used is almost catalytic. Examples of the solvent are aromatic hydrocarbons (e.g. benzene, toluene, xylene), ethers (e.g. 1,4-dioxane, ethylene glycol dimethyl ether), alcohols (e.g. methanol, ethanol), water, etc. These may be used solely or in combination.

After completion of the reaction, the reaction mixture is subjected to ordinary post-treatment such as extraction with an organic solvent and concentration. If desired, any conventional purification procedure such as chromatography or recrystallization may be applied to the product.

Procedure (B)

A compound of the formula:

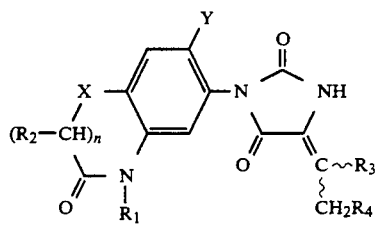

(I-2)

wherein X, Y, R$_1$, R$_2$, R$_3$, R$_4$ and n are each as defined above is prepared by subjecting a compound of the formula:

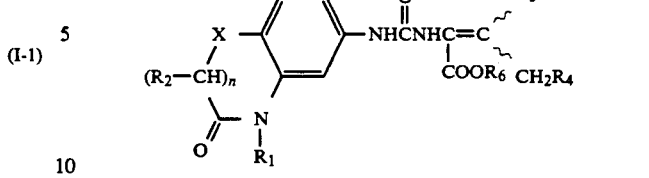

(III)

wherein X, Y, R$_1$, R$_2$, R$_3$, R$_4$, R$_6$ and n are each as defined above to ring closure under the same conditions as that described in the case of Procedure (A).

Procedure (C)

A compound of the formula:

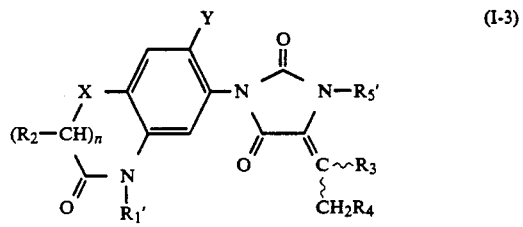

(I-3)

wherein R$_1$' is a C$_1$-C$_6$ alkyl group, a C$_3$-C$_7$ alkenyl group, a C$_3$-C$_7$ alkynyl group, a halo(C$_2$-C$_6$)alkyl group, a halo-(C$_3$-C$_7$)alkenyl group, a cyano(C$_1$-C$_6$)alkyl group, a C$_1$-C$_6$ alkoxy(C$_1$-C$_6$)alkyl group or a C$_1$-C$_6$ alkoxycarbonylmethyl group, R$_5$' is a C$_1$-C$_6$ alkyl group, a C$_3$-C$_7$ alkenyl group, a C$_3$-C$_7$ alkynyl group, a halo(C$_2$-C$_6$)alkyl group or a C$_1$-C$_6$ alkoxycarbonylmethyl group and X, Y, R$_2$, R$_3$, R$_4$ and n are each as defined above is prepared by reacting a compound of the formula:

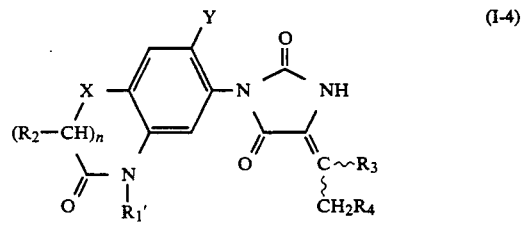

(I-4)

wherein X, Y, R$_1$', R$_2$, R$_3$, R$_4$ and n are each as defined above with a compound of the formula:

R$_5$'—W  (IV)

wherein R$_5$' is as defined above and W is a halogen atom (e.g. chlorine, bromine, iodine) or a sulfonyloxy group (e.g. methanesulfonyloxy, p-toluenesulfonyloxy).

The reaction is usually effected in the presence of an acid-binding agent in an inert solvent at a temperature of about 0° to about 100° C. within about 12 hours. Normally, the compound (IV) and the acid-binding agent are used respectively in amounts of about 0.8 to about 10 equivalents and of about 1.0 to about 1.2 equivalents to one equivalent of the compound (I-4). As the acid-binding agent, there may be used a base such as sodium hydride, sodium hydroxide, potassium carbonate, N,N-diethylaniline or pyridine. Examples of the solvent are aromatic hydrocarbons (e.g. benzene, toluene), ethers (e.g. 1,4-dioxane, tetrahydrofuran, diethyl ether), acid amides (e.g. N,N-dimethylformamide), sulfurous compounds (e.g. dimethylsulfoxide, sulphorane), water, etc. These may be used solely or in combination. If desired, the reaction system may comprise a metal iodide (e.g. sodium iodide, potassium iodide) and/or a phase transfer catalyst (e.g. tetrabutylammonium bromide).

After completion of the reaction, the reaction mixture is subjected to ordinary post-treatment. For instance, the reaction mixture is poured into water, and the precipitated crystals are collected by filtration. Alternatively, the reaction mixture is mixed with water and a water-immiscible organic solvent in combination for extraction, and the extract is concentrated. If desired, any conventional purification procedure such as chromatography or recrystallization may be applied to the product.

Procedure (D)

A compound of the formula:

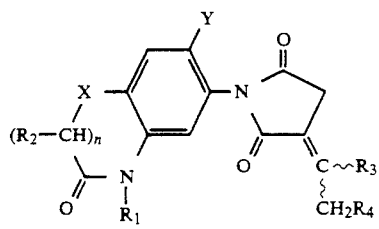
(I-5)

wherein X, Y, $R_1$, $R_2$, $R_3$, $R_4$ and n are each as defined above is prepared by reacting a compound of the formula:

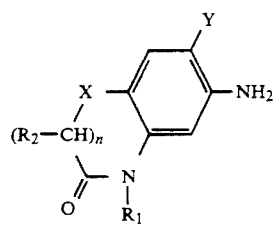
(V)

wherein X, Y, $R_1$, $R_2$ and n are each as defined above with a compound of the formula:

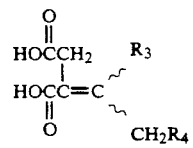
(VI)

wherein $R_3$ and $R_4$ are each as defined above or its inner anhydride.

Normally, the compound (VI) is used in an amount of about 1.0 to about 1.2 equivalents to one equivalent of the compound (V). The reaction is usually effected in the absence or presence of a base without any solvent or in an inert solvent at a temperature of about 30° to about 200° C. for a period of about 1 to about 24 hours. As the base, there may be used an inorganic base (e.g. potassium carbonate, sodium carbonate, sodium hydrogen carbonate) or an organic base (e.g. triethylamine, pyridine, N,N-diethylaniline). Examples of the solvent are benzene, toluene, o-dichlorobenzene, N,N-dimethylformamide, dimethylsulfoxide, acetic acid, etc.

After completion of the reaction, the reaction mixture is subjected to ordinary post-treatment as described in the case of Procedure (A).

Procedure (E)

A compound of the formula:

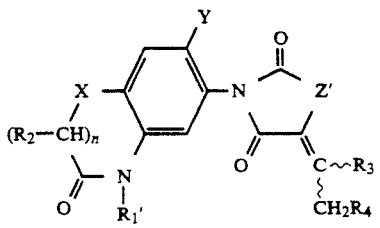
(I-6)

wherein $Z'$ is an oxygen atom, a methylene group or a group of the formula: N—$R_5'$ (in which $R_5'$ is as defined above), X, Y, $R_1'$, $R_2$, $R_3$, $R_4$ and n are each as defined above is prepared by reacting a compound of the formula:

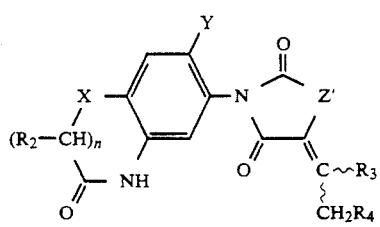
(I-7)

wherein X, Y, $Z'$, $R_2$, $R_3$, $R_4$ and n are each as defined above with a compound of the formula:

$R_1'$—W <span>(VII)</span> wherein $R_1'$ and W are each as defined above.

The reaction may be achieved in the same manner as in the case of procedure (C).

Some typical embodiments for production of the N-phenylimides (I) are illustratively shown in the following examples.

EXAMPLE 1

Preparation of 3-[7-fluoro-4-propargyl-2H-1,4-benzoxazin-3(4H)-on-6-yl]-5-isopropylidene-1,3-oxazolidin-2,4-dione (Compound No. 9)

To a solution of 7-fluoro-6-(1-methoxycarbonyl-2-methyl-2-propenyloxycarbonylamino)-4-propargyl-2H-1,4-benzoxazin-3(4H)-one (10 g) in toluene (100 g), sodium methoxide was added in an amount of 0.05 equivalent to one equivalent of the benzoxazine. The resulting mixture was refluxed for 3 hours, cooled to room temperature, combined with water and extracted with ethyl acetate. The organic layer was washed with water three times, dried over magnesium sulfate and concentrated. The residue was purified by silica gel column chromatography using a mixture of hexane and ethyl acetate as the eluent to give Compound No. 9 (6.1 g). m.p., 194°–198° C.

NMR (solvent: CDCl$_3$, standard: TMS): 7.05 (d, 1H), 6.86 (d, 1H), 4.65–4.70 (4H), 2.30 (s, 3H), 2.05 (s, 3H).

EXAMPLE 2

Preparation of 6-fluoro-5-(5-isopropylidene-1,3-oxazolidine-2,4-dion-3-yl)-3-propargyl-2(3H)-benzothiazolone (Compound No. 40):—

To a solution of 6-fluoro-5-(1-methoxycarbonyl-2-methyl-2-propenyloxycarbonylamino)-3-propargyl-2(3H)-benzothiazolone (10 g) in toluene (100 g), sodium methylate was added in an amount of 0.05 equivalent to one equivalent of the benzothiazolone. The resulting mixture was refluxed for 3 hours, cooled to room temperature, combined with water and extracted with ethyl acetate. The organic layer was purified by silica gel column chromatography to give Compound No. 40 (6.8 g).

NMR (solvent: CDCl$_3$, standard: TMS): 7.36 (d, 1H), 7.18 (d, 1H), 4.65 (d, 2H), 2.30 (4H), 2.05 (s, 3H).

EXAMPLE 3

Preparation of 3-[7-fluoro-4-propargyl-2H-1,4-benzoxazin-3(4H)-on-6-yl]-5-isopropylidenehydantoin (Compound No. 31):—

N-[7-fluoro-4-propargyl-2H-1,4-benzoxazin-3(4H)-on-6-yl]-N'-(1-methoxycarbonyl-1-isopropylidene)methylurea (1.4 g) and DBU (0.5 g) were dissolved in benzene (50 ml). The resulting mixture was refluxed for 10 hours, cooled to room temperature, combined with water and extracted with ethyl acetate. The organic layer was purified by recrystallization from ethanol to give Compound No. 31 (1.1 g).

NMR (solvent: DMSO-d$_6$, standard: TMS): 7.25 (d, 1H), 6.95 (d, 1H), 4.75 (s, 2H), 4.60 (s, 2H), 2.18 (s, 3H), 1.90 (s, 3H).

EXAMPLE 4

Preparation of 1-methyl-3-[7-fluoro-4-propargyl-2H-1,4-bezoxazin-3(4H)-on-6-yl]-5-isopropylidenehydantoin (Compound No. 32):—

3-[7-fluoro-4-propargyl-2H-1,4-bezoxazin-3(4H)-on-6-yl]-5-isopropylidenehydantoin (1.2 g), potassium carbonate (3.0 g) and iodomethane (3.0 g) were dissolved in N,N-dimethylformamide (30 ml), followed by heating at 70° C. for 6 hours. The reaction mixture was allowed to cool, combined with water and extracted with ethyl acetate. The organic layer was purified by silica gel column chromatography using a mixture of toluene and ethyl acetate as the eluent to give Compound No. 32 (1.1 g).

NMR (solvent: CDCl$_3$, standard: TMS): 7.02 (d, 1H), 6.75 (d, 1H), 4.55 (4H), 3.35 (s, 3H), 2.30 (s, 3H), 2.20 (t, 1H) 2.10 (s, 3H).

EXAMPLE 5

Preparation of N-[7-fluoro-4-propargyl-2H-1,4-benzoxazin-3(4H)-on-6-yl]teraconimide (Compound No. 30):—

6-Amino-7-fluoro-4-propargyl-2H-1,4-benzoxazin-3(4H)-one (10 g) and teraconic anhydride (6.3 g) were dissolved in acetic acid (200 ml). The resulting mixture was refluxed for 5 hours, cooled to room temperature, combined with water and extracted with ethyl acetate. The organic layer was purified by silica gel column chromatography using a mixture of hexane and ethyl acetate as the eluent to give Compound No. 30 (13.1 g). m.p., 160°–165° C.

NMR (solvent: CDCl$_3$, standard: TMS): 7.15 (d, 1H), 6.82 (d,1H), 4.60–4.70 (4H), 3.40–3.55 (2H), 2.20–2.50 (4H), 2.00 (s, 3H).

EXAMPLE 6

Preparation of 3-[7-fluoro-4-(2-butenyl)-2H-1,4-benzoxazin-3(4H)-on-6-yl]-5-isopropylidene-1,3-oxazolidine- 2,4-dione (Compound No. 8):—

To a solution of 3-[7-fluoro-2H-1,4-benzoxazin-3(4H)-on-6-yl]-5-isopropylidene-1,3-oxazolidine-2,4-dione (1.1 g), potassium carbonate (0.3 g) and potassium iodide (0.1 g) in N,N-dimethylformamide (50 ml), 1-bromo-2-butene (0.5 g) was added, followed by heating at 70° C. for 4 hours. The reaction mixture was allowed to cool, combined with water and extracted with ethyl acetate. The organic layer was purified by silica gel column chromatography to give Compound No. 8 (1.0 g).

NMR (solvent: CDCl$_3$, standard: TMS): 6.70–7.00 (2H), 5.30–5.70 (2H), 4.60 (s, 2H) 4.30–4.70 (2H), 2.25 (s, 3H), 2.00 (s, 3H), 1.50–1.80 (3H).

In the same manner as above, the N-phenylimides (I) as shown in Table 1 are obtained.

TABLE 1

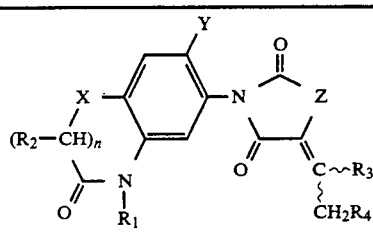

(I)

| Compound No. | X | Y | Z | R$_1$ | R$_2$ | R$_3$ | R$_4$ | n | Physical property |
|---|---|---|---|---|---|---|---|---|---|
| 1 | O | H | O | CH$_2$C≡CH | H | CH$_3$ | H | 1 | *7.10–7.40(3H), 4.70(4H), 2.31(s, 3H), 2.10(s, 3H) |
| 2 | O | F | O | H | H | CH$_3$ | H | 1 | **6.70–7.10(2H), 4.60(s, 2H), 2.20(s, 3H), 1.95(s, 3H) |
| 3 | O | F | O | CH$_3$ | H | CH$_3$ | H | 1 | m.p. 189–193° C. |
| 4 | O | F | O | C$_2$H$_5$ | H | CH$_3$ | H | 1 | **7.40(d, 1H), 7.10(d, 1H), 4.75(s, 2H), 3.90(q, 2H), 2.25(s, 3H), 2.05(s, 3H), 1.19(t, 3H) |
| 5 | O | F | O | (n)C$_3$H$_7$ | H | CH$_3$ | H | 1 | m.p. 147–150° C. **7.00–7.50(2H), 4.70(s, 2H), 3.70(t, 2H), 2.22(s, 3H), 2.00(s, 3H), 1.10–1.80(2H), 0.90(t, 3H) |
| 6 | O | F | O | (i)C$_3$H$_7$ | H | CH$_3$ | H | 1 | $n_D^{22.0}$ 1.5410 |

TABLE 1-continued

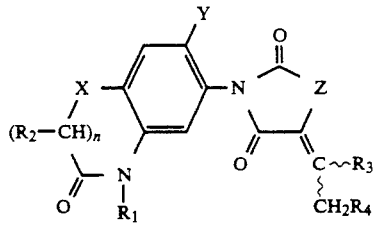

(I)

| Compound No. | X | Y | Z | $R_1$ | $R_2$ | $R_3$ | $R_4$ | n | Physical property |
|---|---|---|---|---|---|---|---|---|---|
| 7 | O | F | O | $CH_2CH=CH_2$ | H | $CH_3$ | H | 1 | m.p. 184–190° C.<br>**7.00–7.40(2H), 5.00–6.50(m, 3H), 4.70(s, 2H),<br>4.40(d, 2H), 2.20(s, 3H), 2.00(s, 3H) |
| 8 | O | F | O | $CH_2CH=CHCH_3$ | H | $CH_3$ | H | 1 | *6.70–7.00(2H), 5.30–5.70(2H), 4.60(s, 2H),<br>4.30–4.70(2H), 2.25(s, 3H), 2.00(s, 3H),<br>1.50–1.80(3H) |
| 9 | O | F | O | $CH_2C\equiv CH$ | H | $CH_3$ | H | 1 | m.p. 194–198° C. |
| 10 | O | F | O | CHC≡CH<br>\|<br>$CH_3$ | H | $CH_3$ | H | 1 | m.p. 88–93° C.<br>*7.60(d, 1H), 6.90(d, 1H),<br>5.80–6.20(m, 1H), 4.69(s, 2H),<br>2.50(d, 1H), 2.30(s, 3H), 2.10(s, 3H),<br>1.60(d, 3H) |
| 11 | O | F | O | $CH_2C\equiv CCH_3$ | H | $CH_3$ | H | 1 | *6.60–7.10(2H), 4.60(s, 2H), 4.50(d, 2H),<br>2.30(s, 3H), 2.00(s, 3H), 1.70(t, 3H) |
| 12 | O | F | O | $CH_2CH_2F$ | H | $CH_3$ | H | 1 | *6.70–7.30(2H), 5.05(t, 1H), 4.20–4.50(2H),<br>4.66(s, 2H), 4.00(t, 1H), 2.28(s, 3H),<br>2.06(s, 3H) |
| 13 | O | F | O | $CH_2CH=CHCl$ | H | $CH_3$ | H | 1 | *6.70–7.00(2H), 5.50–6.50(2H), 4.60(s, 2H),<br>2.25(s, 3H), 2.00(s, 3H) |
| 14 | O | F | O | $CH_2CN$ | H | $CH_3$ | H | 1 | $n_D^{23.1}$ 1.4500 |
| 15 | O | F | O | $CH_2CH_2OCH_3$ | H | $CH_3$ | H | 1 | *7.20(d, 1H), 6.80(d, 1H), 4.60(s, 2H), 3.50–4.20(4H),<br>3.29(s, 3H), 2.25(s, 3H), 2.02(s, 3H) |
| 16 | O | F | O | $CH_2COOCH_3$ | H | $CH_3$ | H | 1 | *6.90(d, 1H), 6.65(d, 1H), 4.70(s, 2H), 4.60(s, 2H),<br>3.75(s, 3H), 2.30(s, 3H), 2.05(s, 3H) |
| 17 | O | H | $CH_2$ | $CH_2C\equiv CH$ | H | $CH_3$ | H | 1 | *6.80–7.20(2H), 4.40–4.70(4H), 3.20–3.50(2H),<br>2.40(s, 3H), 1.95(s, 3H) |
| 18 | O | F | $NCH_2CH_2F$ | $CH_2C\equiv CH$ | H | $CH_3$ | H | 1 | *7.15(d, 1H), 6.95(d, 1H), 4.55–5.55(4H),<br>4.70(s, 2H), 2.42(s, 3H), 2.20(s, 3H) |
| 19 | O | F | $CH_2$ | $CH_2C\equiv CH$ | $CH_3$ | $CH_3$ | H | 1 | *7.10(d, 1H), 6.80(d, 1H), 4.50–4.80(3H),<br>3.40–3.50(2H), 2.30(s, 3H), 2.22(t, 1H),<br>1.91(s, 3H), 1.60(d, 3H) |
| 20 | O | F | O | $CH_2C\equiv CH$ | $CH_3$ | $CH_3$ | H | 1 | *7.05(d, 1H), 6.85(d, 1H), 4.50–4.80(3H),<br>2.30(s, 3H), 2.05(s, 3H), 1.55(d, 3H) |
| 21 | O | F | O | $CH_2C\equiv CH$ | H | H | H | 1 | *7.10(d, 1H), 6.85(d, 1H), 6.00–6.40(1H),<br>4.50–4.70(4H), 1.95(d, 3H) |
| 22 | O | F | O | $CH_2C\equiv CH$ | H | H | $CH_3$ | 1 | *7.05(d, 1H), 6.86(d, 1H), 6.12(t, 1H),<br>4.62(4H), 2.10–2.60(3H), 1.16(t, 3H) |
| 23 | O | F | O | $CH_2C\equiv CH$ | H | $CH_3$ | $CH_3$ | 1 | $n_D^{22.5}$ 1.4684 |
| 24 | O | F | O | $CH_2C\equiv CH$ | H | $CH_3$ | $C_2H_5$ | 1 | $n_D^{23.5}$ 1.4560 |
| 25 | O | F | O | $CH_2C\equiv CH$ | H | $C_2H_5$ | $CH_3$ | 1 | *7.15(d, 1H), 6.90(d, 1H), 4.70(4H),<br>2.80(q, 4H), 1.20(t, 6H) |
| 26 | O | F | $CH_2$ | $CH_3$ | H | $CH_3$ | H | 1 | *6.60–7.00(2H), 4.60(s, 2H), 3.30–3.50(2H),<br>3.30(s, 3H), 2.36(s, 3H), 1.95(s, 3H) |
| 27 | O | F | $CH_2$ | $C_2H_5$ | H | $CH_3$ | H | 1 | *6.70–7.00(2H), 4.58(s, 2H), 3.90(q, 2H),<br>3.20–3.50(broad, 2H), 2.38(s, 3H), 1.90(s, 3H),<br>1.25(t, 3H) |
| 28 | O | F | $CH_2$ | $(n)C_3H_7$ | H | $CH_3$ | H | 1 | **7.00–7.30(2H), 4.70(s, 2H), 3.70(t, 2H),<br>3.40–3.60(broad, 2H), 2.30(s, 3H), 1.90(s, 3H),<br>1.30–1.80(2H), 0.90(t, 3H) |
| 29 | O | F | $CH_2$ | $CH_2CH=CH_2$ | H | $CH_3$ | H | 1 | *6.70–7.00(2H), 4.90–6.20(m, 3H), 4.60(s, 2H),<br>4.45(d, 2H), 3.30–3.50(broad, 2H),<br>2.35(s, 3H), 1.90(s, 3H) |
| 30 | O | F | $CH_2$ | $CH_2C\equiv CH$ | H | $CH_3$ | H | 1 | m.p. 160–165° C. |
| 31 | O | F | NH | $CH_2C\equiv CH$ | H | $CH_3$ | H | 1 | **7.25(d, 1H), 6.95(d, 1H), 4.75(s, 2H),<br>4.60(s, 2H), 2.18(s, 3H), 1.90(s, 3H) |
| 32 | O | F | $NCH_3$ | $CH_2C\equiv CH$ | H | $CH_3$ | H | 1 | *7.02(d, 1H), 6.75(d, 1H), 4.55(4H), 3.35(s, 3H),<br>2.30(s, 3H), 2.20(t, 1H), 2.10(s, 3H) |
| 33 | O | F | $NCH_2CH=CH_2$ | $CH_2C\equiv CH$ | H | $CH_3$ | H | 1 | *7.10(d, 2H), 6.90(d, 1H), 5.00–6.50(m, 3H),<br>4.70(4H), 4.40–4.60(2H), 2.40(s, 3H),<br>2.30(t, 3H), 2.10(s, 3H) |
| 34 | O | F | $NCH_2C\equiv CH$ | $CH_2C\equiv CH$ | H | $CH_3$ | H | 1 | *7.12(d, 1H), 6.90(d, 1H), 4.70(6H),<br>2.40(s, 3H), 2.30(s, 3H) |
| 35 | S | F | O | $CH_3$ | — | $CH_3$ | H | 0 | m.p. 147–150° C. |
| 36 | S | F | O | $C_2H_5$ | — | $CH_3$ | H | 0 | *7.32(d, 1H), 6.95(d, 1H), 3.95(q, 2H),<br>2.30(s, 3H), 2.10(s, 3H), 1.35(t, 3H) |
| 37 | S | F | O | $(n)C_3H_7$ | — | $CH_3$ | H | 0 | m.p. 220–224° C. |

TABLE 1-continued

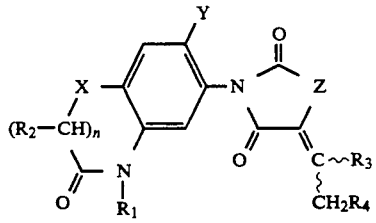
(I)

| Compound No. | X | Y | Z | R₁ | R₂ | R₃ | R₄ | n | Physical property |
|---|---|---|---|---|---|---|---|---|---|
| 38 | S | F | O | (s)C₄H₉ | — | CH₃ | H | 0 | *7.00–7.40(2H), 4.20–4.60(1H), 2.30(s, 3H), 2.10(s, 3H), 1.55(d, 3H), 0.80–1.50(5H) |
| 39 | S | F | O | CH₂CH=CH₂ | — | CH₃ | H | 0 | **7.90(d, 1H), 7.49(d, 1H), 4.80–6.20(m, 3H), 4.50(d, 2H), 2.23(s, 3H), 2.00(s, 3H) |
| 40 | S | F | O | CH₂C≡CH | — | CH₃ | H | 0 | *7.36(d, 1H), 7.18(d, 1H), 4.65(d, 2H), 2.30(4H), 2.05(s, 3H) |
| 41 | S | F | O | CH—C≡CH / CH₃ | — | CH₃ | H | 0 | *7.55(d, 1H), 7.35(d, 1H), 5.50–6.00(m, 1H), 2.30(s, 3H), 2.10(s, 3H), 1.70(d, 3H) |
| 42 | S | F | O | CH₂CH₂OCH₃ | — | CH₃ | H | 0 | m.p. 171.5–173.5° C. |
| 43 | S | F | O | CH₂C≡CH | H | CH₃ | H | 1 | |
| 44 | O | F | CH₂ | (i)C₃H₇ | H | CH₃ | H | 1 | *6.70–7.00(2H), 4.40–4.90(m, 1H), 4.50(s, 2H), 3.30–3.60(broad, 2H), 2.40(s, 3H), 2.00(s, 3H), 1.50(d, 6H) |
| 45 | O | F | O | CH₂OCH₃ | H | CH₃ | H | 1 | *7.20(d, 1H), 6.83(d, 1H), 5.20(s, 2H), 4.60(s, 2H), 3.32(s, 3H), 2.25(s, 3H), 2.00(s, 3H) |
| 46 | O | F | O | CH₂OC₂H₅ | H | CH₃ | H | 1 | *7.21(d, 1H), 6.81(d, 1H), 5.24(s, 2H), 4.60(s, 2H), 3.55(q, 2H), 2.21(s, 3H), 2.00(s, 3H), 1.15(t, 3H) |
| 47 | O | F | NCH₂COCH₃ ‖ O | CH₂C≡CH | H | CH₃ | H | 1 | *7.15(d, 1H), 6.90(d, 1H), 4.65(6H), 3.80(s, 3H), 2.35(s, 3H), 2.05(s, 3H) |
| 48 | O | F | CH₂ | H | H | CH₃ | H | 1 | *6.60–7.00(2H), 4.60(s, 2H), 3.30–3.50(broad, 2H), 2.35(s, 3H), 1.90(s, 3H) |
| 49 | S | F | CH₂ | (s)C₄H₉ | — | CH₃ | H | 0 | *7.30(d, 1H), 7.05(d, 1H), 4.20–4.70(m, 1H), 3.30–3.50(broad, 2H), 2.40(s, 3H), 2.00(s, 3H), 1.50(d, 3H), 0.90(t, 3H) |
| 50 | O | F | CH₂ | CH₂CH=CHCH₃ | H | CH₃ | H | 1 | *6.60–6.90(2H), 5.30–5.70(m, 2H), 4.60(s, 2H), 4.40(d, 2H), 3.30–3.50(broad, 2H), 2.40(s, 3H), 1.90(s, 3H), 1.70(3H) |
| 51 | S | F | O | (i)C₃H₇ | — | CH₃ | H | 0 | |
| 52 | S | F | O | CH₂OCH₃ | — | CH₃ | H | 0 | |
| 53 | S | F | O | CH₂OC₂H₅ | — | CH₃ | H | 0 | |
| 54 | S | F | O | CH₂CN | — | CH₃ | H | 0 | |
| 55 | S | F | CH₂ | CH₃ | — | CH₃ | H | 0 | m.p. 202–205° C. |
| 56 | S | F | CH₂ | C₂H₅ | — | CH₃ | H | 0 | **7.80(d, 1H), 7.40(d, 1H), 3.90(d, 2H), 3.50(broad, 2H), 2.30(s, 3H), 1.90(s, 3H), 1.18(t, 3H) |
| 57 | S | F | CH₂ | (n)C₃H₇ | — | CH₃ | H | 0 | m.p. 128.5–130° C. |
| 58 | S | F | CH₂ | CH₂CH=CH₂ | — | CH₃ | H | 0 | m.p. 173–174.5° C. |
| 59 | S | F | CH₂ | CH₂C≡CH | — | CH₃ | H | 0 | m.p. 238.5–239.8° C. |
| 60 | S | F | CH₂ | CH₂CH=CHCH₃ | — | CH₃ | H | 0 | m.p. 156–158° C. |
| 61 | S | F | CH₂ | CH₂C≡CCH₃ | — | CH₃ | H | 0 | *7.26(d, 1H), 7.05(d, 1H), 4.60(q, 2H), 3.40(broad, 2H) 2.36(s, 3H), 1.94(s, 3H), 1.75(t, 3H) |
| 62 | S | F | CH₂ | CHC≡CH / CH₃ | — | CH₃ | H | 0 | *7.42(d, 1H), 7.26(d, 1H), 5.40–5.90(m, 1H), 3.40(broad, 2H), 2.48(d, 1H), 2.36(s, 3H), 1.92(s, 3H), 1.65(d, 3H) |
| 63 | S | F | CH₂ | CH₂CH=CHCl | — | CH₃ | H | 0 | *7.24(d, 1H), 6.80(d, 1H), 5.00–6.40(2H), 4.20–4.60(2H), 3.40(broad, 2H), 2.35(s, 3H), 1.95(s, 3H) |

Note:
*NMR (solvent, CDCl₃; standard, TMS)
**NMR (solvent, DMSO-d₆; standard, TMS)

The process for preparing the intermediates of the formula:

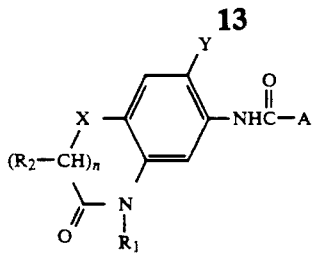

(II) and (III)

wherein A is a group of the formula:

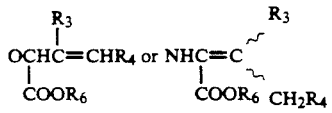

(in which $R_3$, $R_4$ and $R_6$ are each as defined above) and X, Y, $R_1$, $R_2$ and n are each as defined above will be hereinafter explained in detail.

Procedure (F):—

The compound (II) (i.e. A being a group of the formula:

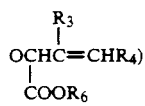

is prepared by reacting a compound of the formula:

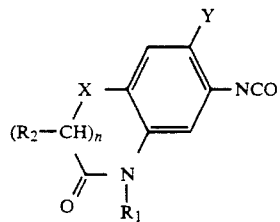

wherein X, Y, $R_1$, $R_2$ and n are each as defined above with a compound of the formula:

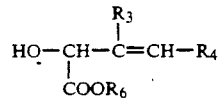

wherein $R_3$, $R_4$ and $R_6$ are each as defined above.

The reaction is performed in the absence or presence of an inert solvent at a temperature of about 0° to about 50° C. instantaneously or within about 12 hours. Normally, the compound (IX) is used in an amount of about 1.0 to about 1.2 equivalents to one equivalent of the compound (VIII). Examples of the solvent are benzene, toluene, xylene, diethyl ether, tetrahydrofuran, 1,4-dioxane, N,N-dimethylformamide, chloroform, carbon tetrachloride, etc. If desired, the reaction system may comprise a catalyst (e.g. triethylamine, N,N-diethlaniline, 1,4-diazabicyclo[2,2,2]octane, DBU).

The compound (VIII) can be prepared by reacting the compound (V) with phosgene. The reaction is performed in an inert solvent and accomplished at a temperature of about 50° C. to the boiling point instantaneously or within about 10 hours. Normally, phosgene is used in an amount of about 3.0 to about 10 equivalents to one equivalent of the compound (V). Examples of the solvent are benzene, toluene, xylene, ethyl acetate or their mixture.

The compound (IX) can be prepared according to the method described in the literature (J.Am.Chem.Soc., 95, 553 (1973)).

Procedure (G):—

The compound (III) (i.e. A being a group of the formula:

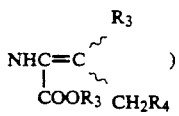

can be prepared by reacting the compound (VIII) with a compound of the formula:

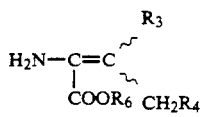

wherein $R_3$, $R_4$ and $R_6$ are each as defined above.

The reaction can be performed under the same conditions as that described in the case of Procedure (F). The compound (X) can be prepared according to the method described in the literature (J.Org.Chem., 32, 1860 (1967)).

Some typical embodiments for production of the compounds (II) and (III) are illustratively shown in the following examples.

EXAMPLE 7

Preparation of 7-fluoro-6-(1-methoxycarbonyl-2-methyl-2-propenyloxycarbonylamino)-4-propargyl-2H-1,4-benzoxazin-3(4H)-one (Compound No. 72):—

To a solution of 7-fluoro-6-isocyanato-4-propargyl-2H-1,4-benzoxazin-3(4H)-one (2.5 g) and methyl 2-hydroxy-3-methyl-3-butenoate (1.3 g) in benzene (50 ml), triethylamine (0.5 g) was added at room temperature. The resulting mixture was refluxed for 1 hour, cooled to room temperature, combined with water and extracted with ethyl acetate. The organic layer was washed with water, dried over magnesium sulfate and concentrated. The residue was purified by silica gel column chromatography using a mixture of toluene and ethyl acetate as the eluent to give Compound No. 72 (2.9 g). $n_D^{25.0}$ 1.4868

NMR (solvent: CDCl$_3$, standard: TMS): 7.90 (d, 1H), 6.75 (d, 1H), 5.00–5.30 (2H), 4.65 (d, 2H), 5.48 (s, 1H), 4.55 (s, 2H), 3.75 (s, 3H), 2.29 (t, 1H), 1.85 (s, 3H).

EXAMPLE 8

Preparation of N-[7-fluoro-4-propargyl-2H-1,4-benzoxazin-3(4H)-on-6-yl]-N'-(1-ethoxycarbonyl-1-isopropylidene)methylurea (Compound No. 80):—

7-Fluoro-6-isocyanato-4-propargyl-2H-1,4-benzoxazin-3(4H)-one (2.5 g) and ethyl 2-amino-3-methyl-2-butenoate (1.4 g) were dissolved in benzene (50 ml). The resulting mixture was stirred at room temperature for 1 hour, combined with water and extracted with ethyl acetate. The organic layer was washed with water, dried over magnesium sulfate and concentrated. The residue was washed with hexane to give Compound No. 80 (2.2 g). m.p., 188.5°–191.5° C.

NMR (solvent: DMSO-$d_6$, standard: TMS): 8.00 (d, 1H), 7.00 (d, 1H), 4.65 (s, 2H), 4.10 (q, 2H), 1.96 (s, 3H), 1.80 (s, 3H), 1.20 (t, 3H).

In the same manner as above, the compounds (II) and (III) as shown in Table 2 are obtained.

TABLE 2

(II) and (III)

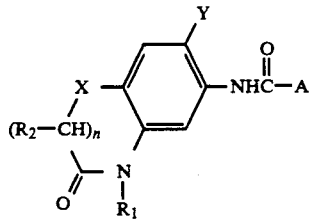

| Compound No. | X | Y | $R_1$ | $R_2$ | A | n | Physical property |
|---|---|---|---|---|---|---|---|
| 64 | O | H | CH$_2$C≡CH | H | OCHC=CH$_2$ with CH$_3$ and COOCH$_3$ | 1 | |
| 65 | O | F | H | H | OCHC=CH$_2$ with CH$_3$ and COOCH$_3$ | 1 | *7.90(d, 1H), 6.75(d, 1H), 5.45(s, 1H), 5.05–5.30(2H), 4.55(s, 2H), 3.75(3H) |
| 66 | O | F | CH$_3$ | H | OCHC=CH$_2$ with CH$_3$ and COOCH$_3$ | 1 | *7.70(d, 1H), 6.70(d, 1H), 5.45(s, 1H), 5.00–5.30(2H), 4.55(s, 2H), 3.75(s, 3H), 3.30(s, 3H), 1.85(s, 3H) |
| 67 | O | F | C$_2$H$_5$ | H | OCHC=CH$_2$ with CH$_3$ and COOCH$_3$ | 1 | |
| 68 | O | F | (n)C$_3$H$_7$ | H | OCHC=CH$_2$ with CH$_3$ and COOCH$_3$ | 1 | |
| 69 | O | F | (i)C$_3$H$_7$ | H | OCHC=CH$_2$ with CH$_3$ and COOCH$_3$ | 1 | |
| 70 | O | F | CH$_2$CH=CH$_2$ | H | OCHC=CH$_2$ with CH$_3$ and COOCH$_3$ | 1 | |
| 71 | O | F | CH$_2$CH=CH—CH$_3$ | H | OCHC=CH$_2$ with CH$_3$ and COOCH$_3$ | 1 | |
| 72 | O | F | CH$_2$C≡CH | H | OCHC=CH$_2$ with CH$_3$ and COOCH$_3$ | 1 | $n_D^{25.0}$ 1.4868 |
| 73 | O | F | CHC≡CH with CH$_3$ | H | OCHC=CH$_2$ with CH$_3$ and COOCH$_3$ | 1 | |
| 74 | O | F | CH$_2$C≡CCH$_3$ | H | OCHC=CH$_2$ with CH$_3$ and COOCH$_3$ | 1 | |

TABLE 2-continued (II) and (III)

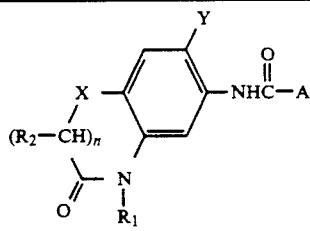

| Compound No. | X | Y | R₁ | R₂ | A | n | Physical property |
|---|---|---|---|---|---|---|---|
| 75 | O | F | CH₂CH₂F | H | OCHC(CH₃)=CH₂ / COOCH₃ | 1 | |
| 76 | O | F | CH₂CH=CHCl | H | OCHC(CH₃)=CH₂ / COOCH₃ | 1 | |
| 77 | O | F | CH₂CN | H | OCHC(CH₃)=CH₂ / COOCH₃ | 1 | |
| 78 | O | F | CH₂CH₂OCH₃ | H | OCHC(CH₃)=CH₂ / COOCH₃ | 1 | |
| 79 | O | F | CH₂COOCH₃ | H | OCHC(CH₃)=CH₂ / COOCH₃ | 1 | |
| 80 | O | F | CH₂C≡CH | H | NHC(CH₃)=CCH₃ / COOC₂H₅ | 1 | m.p. 188.5–191.5° C. |
| 81 | O | F | CH₂C≡CH | CH₃ | OCHC(CH₃)=CH₂ / COOCH₃ | 1 | |
| 82 | O | F | CH₂C≡CH | CH₃ | OCHCH=CH₂ / COOCH₃ | 1 | |
| 83 | O | F | CH₂C≡CH | H | OCHCH=CHCH₃ / COOCH₃ | 1 | |
| 84 | O | F | CH₂C≡CH | H | OCHC(CH₃)=CHCH₃ / COOCH₃ | 1 | |
| 85 | O | F | CH₂C≡CH | H | OCHC(CH₃)=CHC₂H₅ / COOCH₃ | 1 | |
| 86 | O | F | CH₂C≡CH | H | OCHC(C₂H₅)=CHCH₃ / COOCH₃ | 1 | |

TABLE 2-continued (II) and (III)

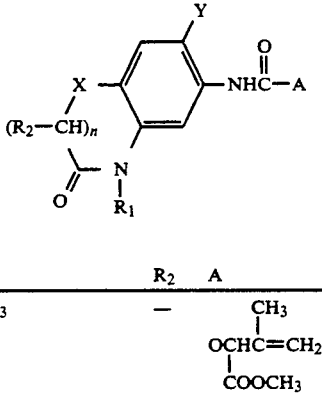

| Compound No. | X | Y | R₁ | R₂ | A | n | Physical property |
|---|---|---|---|---|---|---|---|
| 87 | S | F | CH₃ | — | OCHC=CH₂ with CH₃ and COOCH₃ | 0 | |
| 88 | S | F | C₂H₅ | — | OCHC=CH₂ with CH₃ and COOCH₃ | 0 | |
| 89 | S | F | (n)C₃H₇ | — | OCHC=CH₂ with CH₃ and COOCH₃ | 0 | |
| 90 | S | F | (s)C₄H₉ | — | OCHC=CH₂ with CH₃ and COOCH₃ | 0 | *8.06(d, 1H), 7.15(d, 1H), 5.49(s, 1H), 5.10–5.30(2H), 4.10–4.70(1H), 3.80(s, 3H), 1.50–2.20(8H), 0.90(t, 3H) |
| 91 | S | F | CH₂CH=CH₂ | — | OCHC=CH₂ with CH₃ and COOCH₃ | 0 | |
| 92 | S | F | CH₂C≡CH | — | OCHC=CH₂ with CH₃ and COOCH₃ | 0 | *8.05(d, 1H), 7.12(d, 1H), 5.50(s, 1H), 5.10–5.25(2H), 4.61(d, 2H), 3.75(3H), 2.25(t, 1H), 1.80(s, 3H) |
| 93 | S | F | CHC≡CH / CH₃ | — | OCHC=CH₂ with CH₃ and COOCH₃ | 0 | *8.40(d, 1H), 7.10(d, 1H), 5.50–5.80(1H), 5,55(s, 1H), 5.00–5.30(2H), 3.80(s, 3H), 2.55(t, 1H), 1.90(s, 3H), 1.75(d, 1H) |
| 94 | S | F | CH₂CH₂OCH₃ | — | OCHC=CH₂ with CH₃ and COOCH₃ | 0 | *7.90(d, 1H), 7.10(d, 1H), 5.50(s, 1H), 5.00–5.30(2H), 3.50–4.30(4H), 3.70(s, 3H), 3.30(s, 3H), 1.90(s, 3H) |
| 95 | S | F | CH₂C≡CH | H | OCHC=CH₂ with CH₃ and COOCH₃ | 1 | |
| 96 | O | F | CH₂OCH₃ | H | OCHC=CH₂ with CH₃ and COOCH₃ | 1 | |
| 97 | O | F | CH₂OC₂H₅ | H | OCHC=CH₂ with CH₃ and COOCH₃ | 1 | |
| 98 | S | F | (i)C₃H₇ | — | OCHC=CH₂ with CH₃ and COOCH₃ | 0 | |

TABLE 2-continued

Structure (II) and (III): aromatic ring with Y (top), X attached to (R₂—CH)ₙ, NHC(=O)—A, and N(R₁)C(=O) group.

| Compound No. | X | Y | R₁ | R₂ | A | n | Physical property |
|---|---|---|---|---|---|---|---|
| 99 | S | F | $CH_2OCH_3$ | — | $CH_3$ / $OCHC=CH_2$ / $COOCH_3$ | 0 | |
| 100 | S | F | $CH_2OC_2H_5$ | — | $CH_3$ / $OCHC=CH_2$ / $COOCH_3$ | 0 | |
| 101 | S | F | $CH_2CN$ | — | $CH_3$ / $OCHC=CH_2$ / $COOCH_3$ | 0 | |
| 102 | O | F | $CH_2C\equiv CH$ | H | $CH_3$ / $OCHC=CH_2$ / $COOCH_3$ | 1 | |

Note: *NMR (solvent, $CDCl_3$; standard, TMS)

In the meantime, a compound of the formula:

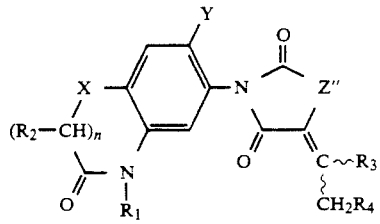

(I-8)

wherein Z" is an oxygen atom or a NH group and X, Y, R₁, R₂, R₃, R₄ and n are each as defined above can be prepared by reacting the compound (VIII) with the compound (IX) or (X) without isolation of the intermediates (II) or (III). The reaction may be performed in the same manner as that in the case of Procedure (A). However, the adoption of a longer reaction time and the use of DBU as a catalyst are recommended.

A typical embodiment for production of the N-phenylimides (I-8) is illustratively shown in the following example.

EXAMPLE 9

Preparation of 3-[7-fluoro-4-propargyl-2H-1,4-benzoxazin-3(4H)-on-6-yl]-5-isopropylidene-1,3-oxazolidine-2,4-dione (Compound No. 9):—

To a solution of 7-fluoro-6-isocyanato-4-propargyl-2H-1,4-benzoxazin-3(4H)-one (2.5 g) and methyl 2-hydroxy-3-methyl-3-butenoate (1.3 g) in benzene (50 ml), DBU (1.5 g) was added at room temperature. The resulting mixture was refluxed for 10 hours, cooled to room temperature, combined with water and extracted with ethyl acetate. The organic layer was washed with water, dried over magnesium sulfate and concentrated. The residue was purified by silica gel column chromatography using a mixture of toluene and ethyl acetate as the eluent to give Compound No. 9 (3.0 g).

In addition to the phenylimides (I), it has been found that the compounds (II) and (III) as the intermediates therefor also show by themselves a herbicidal potency against various weeds with a high selectivity between crop plants and weeds. While some carbamates such as propham (isopropyl N-phenylcarbamate) and some urea derivatives such as fenuron (N-phenyl-N',N'-dimethylurea) are known to be useful as herbicides, these known herbicides are not sufficient in herbicidal potency or have poor selectivity between crop plants and weeds. Therefore, it is notable that the compounds (II) and (III) can produce a significant herbicidal activity against the weeds as stated for the N-phenylimides (I) without any material phytotoxicity on the agricultural crops as cited for the N-phenylimided (I).

For the practical usage of the compounds (I), (II) and (III), they are usually formulated with conventional solid carriers, liquid carriers or diluents as well as surface active agents or auxiliary agents into conventional preparation forms such as emulsifiable concentrates, wettable powders, suspensions and granules. The content of the compound (I), (II) or (III) as the active ingredient in such preparation forms is normally within a range of about 0.05 to about 90% by weight, preferably of about 0.1 to about 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate, synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent usable for emulsification, dispersing or spreading may be of any type, for instance, either anionic or non-ionic. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The compound number of the active ingredient corresponds to the one as shown in Table 1 or 2.

FORMULATION EXAMPLE 1

Fifty parts of any one of Compound Nos. 9, 35, 37, 72 and 90, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of any one of Compound Nos. 4, 51 and 92, 14 parts of polyoxyethylenestyrylphenyl ether, 6 parts of calcium dodecylbenzenesulfonate, 30 parts of xylene and 45 parts of cyclohexanone are well mixed to obtain an emulsifiable concentrate.

FORMULATION EXAMPLE 3

Two parts of any one of Compound Nos. 9, 36, 39 and 40, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of any one of Compound Nos. 7, 37, 40, 53, 72, 90 and 92, 3 parts of polyoxyethylene sorbitan monooleate, 3 parts of carboxymethyl cellulose and 69 parts of water are mixed and pulverized until the particle size becomes less than 5 microns to obtain a suspension.

FORMULATION EXAMPLE 5

Five parts of any one of Compound Nos. 7, 35, 36, 37, 39, 40, 52, 53 and 54, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

The compounds (I), (II) and (III) thus formulated in any suitable preparation form are useful for pre-emergence or post-emergence control of undesired weeds by soil or foliar treatment as well as flood fallowing treatment. These treatments include application to the soil surface prior to or after transplanting, incorporation into the soil, etc. The foliar treatment may be effected by spraying the herbicidal composition containing the compound (I), (II) or (III) over the top of plants. It may also be applied directly to the weeds if care is taken to keep the chemical off the crop foliage.

The compound (I), (II) or (III) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. Furthermore, it may be used as a herbicide applicable to agricultural plowed fields as well as paddy fields. It is also useful as a herbicide to be employed for orchards, pasture land, lawns, forests, non-agricultural fields, etc.

The dosage of the compound (I), (II) or (III) may vary depending oh the prevailing weather conditions, the formulation used, the prevailing season, the mode of application, the soil involved, the crop and weed species, etc. Generally, however, the dosage is from about 0.02 to about 100 grams, preferably from about 0.05 to about 50 grams, of the active ingredient per are. The herbicidal composition of the invention formulated in the form of an emulsifiable concentrate, a wettable powder or a suspension may ordinarily be employed by diluting it with water at a volume of about 1 to about 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the compounds (I), (II) and (III) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, the numeral "0" indicating no material difference as seen in comparison with the untreated plants and the numeral "5" indicating the complete inhibition or death of the test plants.

The compounds as shown in Table 3 were used for comparison.

TABLE 3

| Compound No. | Structure | Remarks |
|---|---|---|
| A | 2,4-difluorophenyl substituted oxazolidine-2,4-dione with isopropylidene | JP-A-62174065 |
| B | 4-chloro-2-fluoro-5-(1-ethoxycarbonylethoxy)phenyl oxazolidine-2,4-dione with isopropylidene | JP-A-62174065 |
| C | 4-chloro-2-fluoro-5-(1-methyl-2-propynyloxy)phenyl oxazolidine-2,4-dione with isopropylidene | JP-A-62174065 |
| D | 4-chloro-2-fluoro-5-isopropoxyphenyl oxazolidine-2,4-dione with isopropylidene | JP-A-62174065 |
| E | 4-chloro-2-fluoro-5-(n-butoxy)phenyl succinimide with isopropylidene | EP-A-0190755 |
| F | 4-chloro-2-fluoro-5-allyloxyphenyl succinimide with isopropylidene | EP-A-0190755 |
| G | 4-chloro-2-fluoro-5-(2-propynyloxy)phenyl N-methyl hydantoin with isopropylidene | EP-A-0262428 |

TABLE 3-continued

| Compound No. | Structure | Remarks |
| --- | --- | --- |
| H | [structure] | U.S. Pat. No. 4,640,707 |
| I | [structure with (s)C₄H₉] | U.S. Pat. No. 4,720,297 |
| J | [structure with CH₂CH=CH₂] | U.S. Pat. No. 4,720,297 |
| K | C₆H₅-NHCO(i)C₃H₇ | Propham |
| L | C₆H₅-NHC(O)N(CH₃)₂ | Fenuron |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate as in Formulation Example 2 or 5 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 4.

TABLE 4

| Compound No. | Dosage (g/are) | Herbicidal activity | | |
| --- | --- | --- | --- | --- |
| | | Japanese millet | Tall morning-glory | Velvetleaf |
| 1 | 20 | 5 | 5 | 5 |
| 2 | 20 | 5 | 4 | 5 |
| 3 | 20 | 4 | 4 | 5 |
| 4 | 20 | 5 | 5 | 5 |
| 5 | 20 | 5 | 5 | 5 |
| 6 | 20 | 5 | 4 | 5 |
| 7 | 20 | 5 | 5 | 5 |
| 8 | 20 | 5 | 5 | 5 |
| 9 | 20 | 5 | 5 | 5 |
| 10 | 20 | 5 | 5 | 5 |
| 12 | 20 | 5 | 4 | 5 |
| 13 | 20 | 4 | 4 | 5 |
| 14 | 20 | 5 | 4 | 5 |
| 15 | 20 | 5 | 4 | 5 |
| 17 | 20 | 5 | 5 | 5 |
| 18 | 20 | 5 | 5 | 5 |
| 19 | 20 | 5 | 5 | 5 |
| 20 | 20 | 5 | 5 | 5 |
| 24 | 20 | 5 | 5 | 5 |
| 25 | 20 | 5 | 4 | 4 |
| 26 | 20 | 5 | 5 | 5 |
| 27 | 20 | 5 | 5 | 5 |
| 28 | 20 | 5 | 5 | 5 |
| 29 | 20 | 5 | 5 | 5 |
| 30 | 20 | 5 | 5 | 5 |
| 31 | 20 | 5 | 5 | 5 |
| 32 | 20 | 5 | 5 | 5 |
| 33 | 20 | 5 | 4 | 4 |
| 34 | 20 | 5 | 5 | 5 |
| 35 | 20 | 5 | 5 | 5 |
| 36 | 20 | 5 | 5 | 5 |
| 37 | 20 | 5 | 5 | 5 |
| 38 | 20 | 5 | 5 | 5 |
| 39 | 20 | 5 | 5 | 5 |
| 40 | 20 | 5 | 5 | 5 |
| 41 | 20 | 5 | 5 | 5 |
| 42 | 20 | 5 | 5 | 5 |
| 43 | 20 | 5 | 5 | 5 |
| 44 | 20 | 5 | 5 | 5 |
| 46 | 20 | 5 | 5 | 5 |
| 48 | 20 | 5 | 5 | 5 |
| 50 | 20 | 5 | 4 | 5 |

TABLE 4-continued

| Compound No. | Dosage (g/are) | Herbicidal activity | | |
|---|---|---|---|---|
| | | Japanese millet | Tall morning-glory | Velvetleaf |
| 51 | 20 | 5 | 5 | 5 |
| 52 | 20 | 5 | 5 | 5 |
| 53 | 20 | 5 | 5 | 5 |
| 54 | 20 | 5 | 5 | 5 |
| 55 | 20 | 5 | 4 | 5 |
| 56 | 20 | 4 | 4 | 5 |
| 57 | 20 | — | 4 | 5 |
| 58 | 20 | 5 | 5 | 5 |
| 59 | 20 | 5 | 5 | 5 |
| 60 | 20 | 5 | 5 | 5 |
| 61 | 20 | 5 | — | 5 |
| 62 | 20 | 5 | — | 5 |
| 63 | 20 | 5 | — | 5 |
| 67 | 40 | 4 | 5 | 5 |
| 68 | 40 | 4 | 4 | 5 |
| 70 | 40 | 4 | 4 | 5 |
| 72 | 40 | 5 | 5 | 5 |
| 80 | 40 | 5 | 5 | 5 |
| 87 | 40 | 4 | 5 | 5 |
| 88 | 40 | 4 | 4 | 5 |
| 89 | 40 | 4 | 4 | 5 |
| 90 | 40 | 5 | 5 | 5 |
| 91 | 40 | 5 | 5 | 5 |
| 92 | 40 | 5 | 5 | 5 |
| 95 | 40 | 5 | 5 | 5 |
| 97 | 40 | 4 | 4 | 5 |
| 98 | 40 | 5 | 5 | 5 |
| 99 | 40 | 4 | 4 | 5 |
| 100 | 40 | 4 | 4 | 5 |
| 101 | 40 | 4 | 4 | 5 |
| 102 | 40 | 5 | 5 | 5 |
| A | 20 | 1 | 0 | 2 |
| K | 40 | 0 | 0 | 0 |

TEST EXAMPLE 2

Cylindrical plastic pots (diameter, 10 cm; height, 10 cm) were filled with upland field soil, and the seeds of radish and velvetleaf were sowed therein and cultivated in a greenhouse for 10 days. A designated amount of the test compound formulated in an emulsifiable concentrate as in Formulation Example 2 or 5 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 5.

TABLE 5

| Compound No. | Dosage (g/are) | Herbicidal activity | |
|---|---|---|---|
| | | Radish | Velvetleaf |
| 1 | 20 | 5 | 5 |
| 2 | 20 | 5 | 5 |
| 3 | 20 | 5 | 5 |
| 4 | 20 | 5 | 5 |
| 5 | 20 | 5 | 5 |
| 6 | 20 | 5 | 5 |
| 7 | 20 | 5 | 5 |
| 8 | 20 | 5 | 5 |

TABLE 5-continued

| Compound No. | Dosage (g/are) | Herbicidal activity | |
|---|---|---|---|
| | | Radish | Velvetleaf |
| 9 | 20 | 5 | 5 |
| 10 | 20 | 5 | 5 |
| 11 | 20 | 5 | 5 |
| 12 | 20 | 5 | 5 |
| 13 | 20 | 5 | 5 |
| 14 | 20 | 5 | 5 |
| 15 | 20 | 5 | 5 |
| 17 | 20 | 5 | 5 |
| 18 | 20 | 5 | 5 |
| 19 | 20 | 5 | 5 |
| 20 | 20 | 5 | 5 |
| 22 | 20 | 5 | 5 |
| 23 | 20 | 5 | 5 |
| 24 | 20 | 5 | 5 |
| 25 | 20 | 5 | 5 |
| 26 | 20 | 5 | 5 |
| 27 | 20 | 5 | 5 |
| 28 | 20 | 5 | 5 |
| 29 | 20 | 5 | 5 |
| 30 | 20 | 5 | 5 |
| 31 | 20 | 5 | 5 |
| 32 | 20 | 5 | 5 |
| 33 | 20 | 5 | 5 |
| 34 | 20 | 5 | 5 |
| 35 | 20 | 5 | 5 |
| 36 | 20 | 5 | 5 |
| 37 | 20 | 5 | 5 |
| 38 | 20 | 5 | 5 |
| 39 | 20 | 5 | 5 |
| 40 | 20 | 5 | 5 |
| 41 | 20 | 5 | 5 |
| 42 | 20 | 5 | 5 |
| 43 | 20 | 5 | 5 |
| 44 | 20 | 5 | 5 |
| 46 | 20 | 5 | 5 |
| 47 | 20 | 5 | 5 |
| 48 | 20 | 5 | 5 |
| 49 | 20 | 5 | 5 |
| 50 | 20 | 5 | 5 |
| 51 | 20 | 5 | 5 |
| 52 | 20 | 5 | 5 |
| 53 | 20 | 5 | 5 |
| 54 | 20 | 5 | 5 |
| A | 20 | 2 | 5 |

TEST EXAMPLE 3

Vats (17 cm×24 cm×7 cm) were filled with upland field soil, and the seeds of corn, tall morningglory, common cocklebur, velvetleaf, black nightshade and green foxtail were sowed therein and cultivated for 16 days in a greenhouse. A designated amount of the test compound formulated in a wettable powder as in Formulation Example 1 was diluted with water containing a spreading agent, and the dilution was sprayed over the foliage of the test plants by means of a small hand sprayer at a spray volume of 5 liters per are. The test plants were further grown in the greenhouse for 18 days, and the herbicidal activity was examined. At the time of the application, the test plants were generally at the 1 to 3 leaf stage and in 5 to 29 cm height, although the growing stage of the test plants varied depending on their species. The results are shown in Table 6.

TABLE 6

| Compound No. | Dosage (g/are) | Herbicidal activity | | | | | Phytotoxicity Corn |
|---|---|---|---|---|---|---|---|
| | | Tall morning-glory | Common cocklebur | Velvet-leaf | Black night-shade | Green foxtail | |
| 6 | 2.5 | 4 | — | 4 | 4 | — | 1 |
| 28 | 0.63 | 5 | 5 | — | 4 | — | 1 |
| 34 | 0.63 | 5 | — | — | 5 | 4 | 1 |
| 80 | 2.5 | 5 | 5 | — | — | 4 | 1 |

TABLE 6-continued

| Compound No. | Dosage (g/are) | Herbicidal activity | | | | | Phytotoxicity Corn |
|---|---|---|---|---|---|---|---|
| | | Tall morning-glory | Common cocklebur | Velvet-leaf | Black night-shade | Green foxtail | |
| 90 | 2.5 | 5 | 5 | 5 | 5 | — | 1 |
| L | 2.5 | 3 | 1 | — | — | 2 | 3 |

TEST EXAMPLE 4

Vats (17 cm×24 cm×7 cm) were filled with upland field soil, and the seeds of tall morningglory, common cocklebur, velvetleaf and black nightshade were sowed therein and cultivated in a greenhouse. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 5 liters per are. The test plants were further grown in the greenhouse for 18 days, and the herbicidal activity was examined. At the time of the application, the test plants were generally at the 1 to 4 leaf stage and in 5 to 30 cm height, although the growing stage of the test plants varied depending on their species. The results are shown in Table 7.

TABLE 7

| Compound No. | Dosage (g/are) | Herbicidal activity | | | |
|---|---|---|---|---|---|
| | | Tall morning-glory | Common cocklebur | Velvet-leaf | Black night-shade |
| 1 | 2.5 | 5 | — | 5 | 5 |
| | 0.63 | 4 | — | 5 | 5 |
| 2 | 2.5 | 5 | 5 | — | 5 |
| 4 | 2.5 | 5 | 5 | 5 | 5 |
| | 0.63 | 4 | — | 4 | 5 |
| 5 | 2.5 | 5 | 5 | 5 | 5 |
| | 0.63 | 5 | 5 | 5 | 5 |
| 7 | 2.5 | 5 | 5 | 5 | 5 |
| 8 | 0.63 | 5 | 5 | 5 | 5 |
| 9 | 2.5 | 5 | 5 | 5 | 5 |
| | 0.63 | 5 | 4 | 5 | 5 |
| 10 | 2.5 | 5 | 5 | 5 | 5 |
| | 0.63 | 5 | 5 | 5 | 5 |
| 12 | 2.5 | 5 | 5 | — | 5 |
| | 0.63 | 5 | 5 | — | 5 |
| 13 | 0.63 | 5 | 5 | 5 | 5 |
| 14 | 2.5 | 5 | — | 5 | 4 |
| 15 | 2.5 | — | — | 4 | 4 |
| 17 | 2.5 | 5 | — | 5 | 5 |
| 19 | 2.5 | 5 | 5 | 5 | 5 |

TABLE 7-continued

| Compound No. | Dosage (g/are) | Herbicidal activity | | | |
|---|---|---|---|---|---|
| | | Tall morning-glory | Common cocklebur | Velvet-leaf | Black night-shade |
| | 0.63 | 5 | — | 5 | 5 |
| 20 | 2.5 | 5 | 5 | 5 | 5 |
| | 0.63 | 5 | — | 5 | 5 |
| 23 | 0.63 | 5 | — | 5 | 5 |
| 24 | 0.63 | 5 | — | 5 | 5 |
| 26 | 2.5 | 5 | — | 5 | 5 |
| 27 | 2.5 | 5 | 5 | 5 | 5 |
| 28 | 2.5 | 5 | — | 5 | 5 |
| 29 | 2.5 | 5 | 5 | 5 | 5 |
| | 0.63 | 5 | 4 | 5 | 5 |
| 30 | 0.63 | 5 | 4 | 5 | 5 |
| 31 | 2.5 | 4 | 5 | 5 | 5 |
| 32 | 2.5 | 5 | 5 | 5 | 5 |
| | 0.63 | 5 | 5 | 5 | 5 |
| 33 | 2.5 | 5 | — | — | 5 |
| 34 | 2.5 | 5 | — | — | 5 |
| 35 | 2.5 | 4 | — | 5 | 5 |
| 36 | 2.5 | 5 | 5 | 5 | 5 |
| | 0.63 | 5 | 5 | 5 | 5 |
| 37 | 2.5 | 5 | 5 | 5 | 5 |
| | 0.63 | 5 | — | 5 | 5 |
| 38 | 0.63 | 5 | — | 5 | 5 |
| 39 | 2.5 | 5 | 5 | 5 | 5 |
| | 0.63 | 5 | 5 | 5 | 5 |
| 40 | 0.63 | 5 | 5 | 5 | 5 |
| 41 | 2.5 | 5 | 5 | 5 | 5 |
| | 0.63 | 5 | 5 | 5 | 5 |
| 42 | 2.5 | 5 | 5 | 5 | 5 |
| | 0.63 | 5 | 5 | 5 | 5 |
| 72 | 0.63 | 5 | 5 | 5 | 5 |
| 90 | 0.63 | 4 | — | 5 | — |

TEST EXAMPLE 5

Vats (17 cm×24 cm×7 cm) were filled with upland field soil, and the seeds of tall morningglory, velvetleaf, black nightshade, barnyardgrass, johnsongrass, green foxtail, soybean, cotton, corn and rice plant were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were further grown in a greenhouse for 18 days, and the herbicidal activity was examined. The results are shown in Table 8.

plants were grown for additional 20 days in the greenhouse, and the herbicidal activity was examined. The results are shown in Table 10.

TABLE 8

| Compound No. | Dosage (g/are) | Herbicidal activity | | | | | | Phytotoxicity | | | |
|---|---|---|---|---|---|---|---|---|---|---|---|
| | | Tall morning-glory | Velvet-leaf | Black night-shade | Barnyard-grass | Johnson-grass | Green foxtail | Soy-bean | Cotton | Corn | Rice plant |
| 1 | 10 | 5 | 4 | — | — | — | 5 | 0 | — | 0 | 1 |
| 5 | 5 | — | 5 | — | — | 4 | 5 | 0 | 0 | 0 | 0 |
| 9 | 2.5 | 4 | 5 | — | — | — | 5 | 1 | — | 0 | — |
| 10 | 5 | — | 5 | 5 | 4 | 5 | 5 | 1 | 1 | — | — |
| 12 | 5 | — | 4 | 5 | — | 4 | — | 0 | 1 | 0 | 1 |
| 18 | 10 | 5 | 4 | — | — | — | 4 | 0 | 0 | 0 | 1 |
| 20 | 10 | — | 5 | 5 | — | — | 5 | 1 | — | 1 | 1 |
| 23 | 10 | — | 4 | 4 | 4 | 5 | 4 | 0 | 0 | 0 | 0 |
| 24 | 10 | 5 | 4 | 4 | — | — | 5 | 0 | — | 0 | 0 |
| 30 | 5 | 5 | 5 | 5 | 4 | 4 | — | — | — | 1 | — |
| 32 | 5 | — | — | 5 | — | 4 | 5 | 1 | — | 1 | 1 |
| 36 | 5 | — | 4 | 4 | — | 4 | 4 | 1 | 0 | 0 | 1 |
| 39 | 5 | — | 5 | 4 | 4 | 4 | 4 | — | 0 | 0 | 0 |
| 40 | 2.5 | — | 5 | 5 | — | — | 4 | 1 | — | 0 | 1 |
| 41 | 5 | — | 5 | 5 | 4 | 5 | 4 | — | — | 1 | 1 |
| 42 | 5 | 4 | 5 | 4 | 4 | 5 | 5 | 1 | 0 | 1 | 1 |
| 72 | 5 | — | 4 | — | — | 4 | 5 | 0 | — | 0 | — |
| B | 10 | 2 | 3 | 0 | 0 | 0 | 0 | 0 | 0 | 0 | 0 |

TEST EXAMPLE 6

Cylindrical plastic pots (diameter, 8 cm; height, 12 cm) were filled with paddy field soil, and the seeds of barnyardgrass (*Echinochloa oryzicola*) and broad-leaved weeds (i.e. common falsepimpernel, indian toothcup, waterwort) were sowed in 1 to 2 cm depth. Water was poured therein to make a flooded condition. Tubers of arrowhead were transplanted therein in 1 to 2 cm depth and rice plants at 2.5 leaf stage were transplanted. The test plants were grown in a greenhouse. Six days thereafter (at that time weeds began to germinate), a designated amount of the test compound formulated in an emulsifiable concentrate as in Formulation Example 2 or 5 and diluted with water (5 ml) was applied to the pots by perfusion. The test plants were grown for additional 20 days in the greenhouse, and the herbicidal activity was examined. The results are shown in Table 9.

TABLE 9

| Compound No. | Dosage (g/are) | Phyto-toxicity Rice plant | Herbicidal activity | | |
|---|---|---|---|---|---|
| | | | Barn-yard-grass | Broad-leaved weed | Arrow-head |
| 36 | 0.63 | 0 | 5 | 5 | 5 |
| 39 | 0.63 | — | 5 | 5 | 5 |
| 40 | 0.63 | — | 5 | 5 | 5 |
| 51 | 0.63 | — | 5 | 5 | 5 |
| A | 0.63 | 0 | 0 | 1 | 0 |

TEST EXAMPLE 7

Cylindrical plastic pots (diameter, 8 cm; height, 12 cm) were filled with paddy field soil, and the seeds of barnyardgrass (*Echinochloa oryzicola*) were sowed in 1 to 2 cm depth. Water was poured therein to make a flooded condition. The test plants were grown in a greenhouse. Six days thereafter (at that time weeds began to germinate), a designated amount of the test compound formulated in an emulsifiable concentrate as in Formulation Example 2 or 5 and diluted with water (5 ml) was applied to the pots by perfusion. The test

TABLE 10

| Compound No. | Dosage (g/are) | Herbicidal activity |
|---|---|---|
| 1 | 10 | 5 |
| 3 | 10 | 5 |
| 4 | 10 | 5 |
| 5 | 10 | 5 |
| 6 | 10 | 5 |
| 8 | 10 | 5 |
| 9 | 10 | 5 |
| 10 | 10 | 5 |
| 11 | 10 | 5 |
| 12 | 10 | 5 |
| 13 | 10 | 5 |
| 14 | 10 | 5 |
| 17 | 10 | 5 |
| 18 | 10 | 5 |
| 19 | 10 | 5 |
| 20 | 10 | 5 |
| 23 | 10 | 5 |
| 24 | 10 | 5 |
| 25 | 10 | 5 |
| 26 | 10 | 5 |
| 27 | 10 | 5 |
| 28 | 10 | 5 |
| 29 | 10 | 5 |
| 30 | 10 | 5 |
| 31 | 10 | 5 |
| 32 | 10 | 5 |
| 33 | 10 | 5 |
| 34 | 10 | 5 |
| 35 | 10 | 5 |
| 36 | 10 | 5 |
| 37 | 10 | 5 |
| 39 | 10 | 5 |
| 41 | 10 | 5 |
| 42 | 10 | 5 |
| 44 | 10 | 5 |
| 48 | 10 | 5 |
| 72 | 10 | 5 |
| 80 | 10 | 5 |

TEST EXAMPLE 8

Wagner pots (1/5000 a) were filled with paddy field soil, and the seeds of barnyardgrass (*Echinochloa oryzicola*), hardstem bulrush and broad-leaved weeds (i.e. common falsepimpernel, indian toothcup, waterwort) were sowed in 1 to 2 cm depth. Water was poured therein to make a flooded condition, and rice plant at 3 leaf stage were transplanted. Test plants were grown in a greenhouse. 5 days thereafter (at that time weeds began to germinate), a designated amount of the test compound formulated in an emulsifiable concentrate as in Formulation Example 2 or 5 was diluted with water (10 ml) and applied to the pots by perfusion, and the depth of water was kept 4 cm. Since the next day of the treatment, water was leaked 3 cm/day for two days. The test plants were grown for additional 20 days in the greenhouse, and the herbicidal activity was examined. The results are shown in Table 11.

TABLE 11

| Compound No. | Dosage (g/are) | Phytotoxicity Rice plant | Herbicidal activity | | |
|---|---|---|---|---|---|
| | | | Barnyardgrass | Hardstem bulrush | Broadleaved weed |
| 28 | 2.5 | 1 | 5 | 5 | 5 |
| | 0.63 | 0 | 5 | — | 5 |
| 29 | 2.5 | 1 | 5 | 5 | 5 |
| | 0.63 | 0 | 5 | 5 | 5 |
| 33 | 2.5 | 0 | 5 | 5 | 5 |
| | 0.63 | 0 | 5 | — | 5 |
| 34 | 2.5 | 1 | 5 | 5 | 5 |
| | 0.63 | 0 | 5 | — | 5 |

TEST EXAMPLE 9

Vats (17 cm×24 cm×7 cm) were filled with upland field soil, and the seeds of sugar beet, wheat, ladysthumb, catchweed bedstraw and pansy were sowed therein and cultivated in a greenhouse. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 5 liters per are. The test plants were further grown in the greenhouse for 18 days, and the herbicidal activity was examined. At the time of the application, the test plants were generally at the 1 to 4 leaf stage and in 1 to 20 cm height. The results are shown in Table 12.

TABLE 12

| Compound No. | Dosage (g/are) | Herbicidal activity | | | Phytotoxicity | |
|---|---|---|---|---|---|---|
| | | Ladysthumb | Catchweed bedstraw | Pansy | Sugar beet | Wheat |
| 9 | 0.08 | 5 | 5 | 5 | 1 | 1 |
| | 0.02 | — | — | 5 | 0 | 0 |
| 39 | 0.08 | 5 | 5 | 5 | 1 | 1 |
| | 0.02 | — | 4 | — | 0 | 0 |
| A | 20 | 0 | 1 | 2 | 1 | 2 |
| B | 1.25 | 2 | 2 | 4 | 1 | 1 |
| C | 0.32 | — | 3 | 3 | 3 | 3 |
| | 0.08 | — | 2 | 2 | 3 | 2 |
| D | 0.32 | — | 3 | — | 3 | 2 |
| | 0.08 | 2 | 2 | — | 0 | 2 |
| E | 1.25 | — | 2 | — | 2 | 2 |
| | 0.32 | — | 2 | — | 1 | 1 |
| F | 0.32 | — | 2 | — | 4 | 2 |
| | 0.08 | — | 0 | — | 4 | 1 |
| G | 0.32 | 3 | 0 | 3 | 2 | 1 |
| | 0.08 | 2 | 0 | 2 | 2 | 0 |
| H | 0.08 | 5 | 2 | 5 | 5 | — |
| | 0.02 | 3 | 1 | 3 | 4 | — |
| I | 0.08 | — | 4 | 3 | 5 | — |
| | 0.02 | — | 0 | 0 | 5 | — |
| J | 0.08 | 4 | — | — | 4 | 2 |
| | 0.02 | 3 | — | — | 3 | 2 |

TEST EXAMPLE 10

Vats (17 cm×24 cm×7 cm) were filled with upland field soil, and the seeds of ladysthumb, redroot pigweed, wild mustard, common lambsquarters, persian speedwell, pansy, wheat, barley and sugar beet were sowed in 1 to 2 cm depth. A designated amount of the test compound formulated in a wettable powder as in Formulation Example 1 was diluted with water, and the dilution was sprayed onto the soil surface by means of a small hand sprayer at a spray volume of 10 liters per are. The test plants were grown in a greenhouse for 18 days, and the herbicidal activity was examined. The results are shown in Table 13.

TABLE 13

| Compound No. | Dosage (g/are) | Herbicidal activity | | | | | | Phytotoxicity | | |
|---|---|---|---|---|---|---|---|---|---|---|
| | | Ladysthumb | Redrood pigweed | Wild mustard | Common lambsquarters | Persian speedwell | Pansy | Wheat | Barley | Sugar beet |
| 4 | 2.5 | 5 | 5 | — | 5 | 5 | 5 | 1 | 1 | — |
| 6 | 2.5 | — | — | — | 5 | — | 5 | 0 | 0 | 1 |
| 9 | 0.63 | 4 | 4 | 4 | 4 | — | 5 | 1 | 1 | 1 |
| 26 | 2.5 | — | — | — | 5 | 5 | 5 | 0 | 1 | 1 |
| 28 | 0.63 | — | — | — | 5 | 5 | — | 0 | 0 | 0 |
| 30 | 0.63 | 5 | 5 | 5 | 5 | — | 5 | 1 | 1 | — |
| 38 | 0.63 | — | 5 | — | 5 | — | — | — | — | 1 |
| 40 | 2.5 | — | — | — | 5 | — | 5 | — | — | 1 |
| B | 2.5 | 2 | — | — | — | 0 | — | 0 | 1 | 3 |
| C | 2.5 | — | — | 2 | — | 3 | 2 | — | — | 1 |
| D | 2.5 | 2 | — | 2 | — | 0 | 3 | — | — | — |
| H | 0.64 | 5 | — | — | — | 3 | — | 2 | 2 | 5 |
| | 0.16 | 3 | — | — | — | 0 | 4 | — | — | 4 |
| I | 2.5 | — | — | 5 | — | 4 | 5 | — | 2 | 5 |
| | 0.64 | — | — | 3 | — | 3 | 3 | — | — | 2 |
| J | 2.5 | — | — | — | — | 5 | 5 | 2 | — | 5 |
| | 0.64 | — | — | — | — | 2 | 2 | — | — | 5 |

What is claimed is:

1. A compound of the formula:

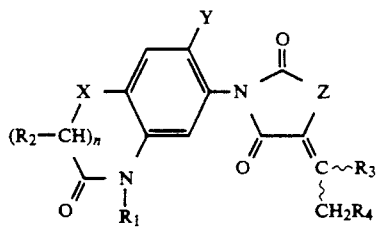

wherein:

X is an oxygen atom or a sulfur atom;

Y is a hydrogen atom or a fluorine atom;

Z is a methylene group or a group of the formula: N—$R_5$ (in which $R_5$ is a hydrogen atom, a $C_1$-$C_6$ alkyl group, a $C_3$-$C_7$ alkenyl group, a $C_3$-$C_7$ alkynyl group, a halo($C_2$-$C_6$)alkyl group or a $C_1$-$C_6$ alkoxycarbonylmethyl group);

$R_1$ is a hydrogen atom, a $C_1$-$C_6$ alkyl group, a $C_3$-$C_7$ alkenyl group, a $C_3$-$C_7$ alkynyl group, a halo($C_2$-$C_6$)alkyl group, a halo ($C_3$-$C_7$)alkenyl group, a cyano($C_1$-$C_6$)alkyl group, a $C_1$-$C_6$ alkoxy($C_1$-$C_6$)alkyl group or a $C_1$-$C_6$ alkoxycarbonylmethyl group;

$R_2$ is a hydrogen atom or a $C_1$-$C_6$ alkyl group;

$R_3$ and $R_4$ are, the same or different, each a hydrogen atom or a $C_1$-$C_6$ alkyl group; and n is an integer of 0 to 1.

2. The compound according to claim 1, wherein Z is a methylene group.

3. The compound according to claim 1, wherein Z is a group of the formula: N—$R_5$.

4. N-(7-fluoro-4-methyl-2H-1,4-benzoxazin-3(4H)-on-6-yl)-teraconimide.

5. N-(7-fluoro-4-propyl-2H-1,4-benzoxazin-3(4H)-on-6-yl)-teraconimide.

6. N-(7-fluoro-4-propargyl-2H-1,4-benzoxazin-3(4H)-on-6-yl)-teraconimide.

7. A herbicidal composition which comprises as an active ingredient a herbicidally effective amount of the compound according to claim 1, and inert carrier or diluent.

8. A method for controlling the growth of undesired weeds, which comprises applying a herbicidally effective amount of the compound according to claim 1 and inert carrier or diluent to an area where the undesired weeds grow or will grow.

* * * * *